(12) United States Patent
Macdonald et al.

(10) Patent No.: US 6,489,322 B1
(45) Date of Patent: Dec. 3, 2002

(54) AMIDINE DERIVATIVES AS INHIBITORS OF NITRIC OXIDE SYNTHASE

(75) Inventors: James Macdonald, Rochester, NY (US); James Matz, Rochester, NY (US); William Shakespeare, Framingham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/068,945

(22) PCT Filed: Apr. 28, 1998

(86) PCT No.: PCT/SE98/00785

§ 371 (c)(1),
(2), (4) Date: May 21, 1998

(87) PCT Pub. No.: WO98/50382

PCT Pub. Date: Nov. 12, 1998

(30) Foreign Application Priority Data

May 5, 1997 (SE) ................................................ 9701681

(51) Int. Cl.⁷ ........................ A61K 31/55; A61P 25/00; C07D 267/14
(52) U.S. Cl. .................. 514/211.09; 540/552
(58) Field of Search ....... 514/211.09; 540/552

(56) References Cited

U.S. PATENT DOCUMENTS 5,807,886 A * 9/1998 MacDonald et al. ........ 514/438
6,117,898 A * 9/2000 MacDonald et al. ........ 514/438

FOREIGN PATENT DOCUMENTS

| WO | 95/05363 | 2/1995 |
|---|---|---|
| WO | 95/09619 | 4/1995 |
| WO | 95/11231 | 4/1995 |
| WO | 96/01817 | 1/1996 |
| WO | 96/24588 | 8/1996 |
| WO | 97/06158 | 2/1997 |
| WO | 97/17344 | 5/1997 |

OTHER PUBLICATIONS

Bredt et al, "Isolation of nitric oxide synthetase, a calmodulin–requiring enzyme," Proc. Natl. Acad. Sci., vol. 87, pp. 682–685 (1990).

Pollock et al, "Purification and characterization of particulate endothelium . . . ," Proc. Natl. Acad. Sci., vol. 88, pp. 10480–10484 (1991).

* cited by examiner

Primary Examiner—Brenda Coleman
(74) Attorney, Agent, or Firm—Nixon & Vanderhye

(57) ABSTRACT

There are provided novel compounds of formula (I)

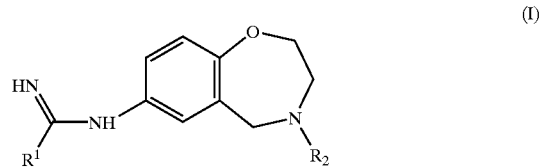

wherein $R^1$ represents a 2-thienyl or 3-thienyl ring and $R^2$ represents hydrogen or C 1 to 4 alkyl and optical isomers and racemates thereof and pharmaceutically acceptable salts thereof; together with processes for their preparation, compositions containing them and their use in therapy. The compounds are selective inhibitors of the neuronal isoform of nitric oxide synthase.

23 Claims, No Drawings

AMIDINE DERIVATIVES AS INHIBITORS OF NITRIC OXIDE SYNTHASE

This application is a national stage entry under 35 U.S.C § of PCT/SE98/00785, filed Apr. 28, 1998.

FIELD OF THE INVENTION

This invention relates to new amidine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been implicated in the pathogenesis of inflammatory diseases. Specific regulation of these enzymes should therefore offer considerable potential in the treatment of a wide variety of disease states.

Compounds of various structures have been described as inhibitors of NOS and their use in therapy has been claimed. See, for example, WO 95/09619 (The Wellcome Foundation) and WO 95/11231 (G. D. Searle). The applicant has previously disclosed in WO 95/05363 and WO 96/01817 amidine derivatives which are NOS inhibitors which display some selectivity for inhibition of the neuronal enzyme, ncNOS.

We now disclose a group of amidines that are within the generic scope of WO 96/01817, but which are not specifically exemplified in WO 96/01817. These compounds display surprisingly advantageous properties and are the subject of the present application.

DISCLOSURE OF THE INVENTION

According to the invention we provide a compound of formula (I)

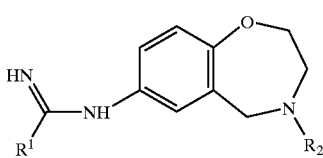

(I)

wherein:
  $R^1$ represents a 2-thienyl or 3-thienyl ring;
  and R2 represents hydrogen or C 1 to 4 alkyl;
  and optical isomers and racemates thereof and pharmaceutically acceptable salts thereof.
  Preferably $R^1$ represents 2-thienyl.
  Preferably $R^2$ represents hydrogen, methyl or 2-propyl.
  Particularly preferred compounds of the invention include:
N-(4-methyl-2,3,4,5-tetrahydro-1,4-benzoxazepin-7-yl)-2-thiophenecarboximidamide;
N-(4-ethyl-2,3,4,5-tetrahydro-1,4-benzoxazepin-7-yl))-2-thiophenecarboximidamide;
N-(4-propyl-2,3,4,5-tetrahydro-1,4-benzoxazepin-7-yl)-2-thiophenecarboximidamide;
N-(4-isopropyl-2,3,4,5-tetrahydro-1,4-benzoxazepin-7-yl)-2-thiophenecarboximidamide;
N-(2,3,4,5-tetrahydro-1,4-benzoxazepin-7-yl)-2-thiophenecarboximidamide;
N-(2,3,4,5-tetrahydro-1,4-benzoxazepin-7-yl)-3-thiophenecarboximidamide;
N-(4-methyl-2,3,4,5-tetrahydro-1,4-benzoxazepin-7-yl)-3-thiophenecarboximidamide; and pharmaceutically acceptable salts thereof.

More especially preferred compounds of the invention include:
N-(4-methyl-2,3,4,5-tetrahydro-1,4-benzoxazepin-7-yl)-2-thiophenecarboximidamide;
N-(4-isopropyl-2,3,4,5-tetrahydro-1,4-benzoxazepin-7-yl)-2-thiophenecarboximidamide;
N-(2,3,4,5-tetrahydro-1,4-benzoxazepin-7-yl)-2-thiophenecarboximidamide; and pharmaceutically acceptable salts thereof.

Unless otherwise indicated, the term "C 1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

According to the invention, we further provide a process for the preparation of compounds of formula (I), and optical isomers and racemates thereof and pharmaceutically acceptable salts thereof, which comprises:
  (a) preparing a compound of formula (I) by reacting a corresponding compound of formula (II)

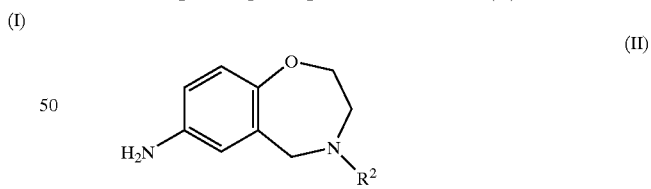

(II)

wherein $R^2$ is as defined above,
  with a compound of formula (III) or an acid addition salt thereof

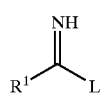

(III)

wherein $R^1$ is as defined above and L is a leaving group;
  (b) preparing a compound of formula (I) by reacting a corresponding compound of formula (IV)

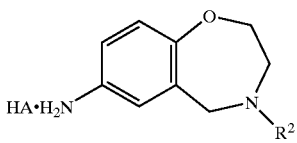

wherein $R^2$ is as defined above and HA is an acid, with a compound of formula (V)

wherein $R^1$ is as defined above;

(c) preparing a compound of formula (I) in which R2 represents C 1 to 4 alkyl by reacting a corresponding compound of formula (I) in which $R^2$ represents hydrogen with a compound of formula (VI)

wherein $R^3$ represents C 1 to 4 alkyl and L is a leaving group; or (d) preparing a compound of formula (I) in which $R^2$ represents methyl by reacting a corresponding compound of formula (I) in which $R^2$ represents hydrogen with formaldehyde and formic acid;

and where desired or necessary converting the resultant compound of formula (I), or another salt thereof, into a pharmaceutically acceptable salt thereof, or vice versa, and where desired converting the resultant compound of formula (I) into an optical isomer thereof In process (a), the reaction will take place on stirring a mixture of the reactants in a suitable solvent, for example, N-methyl-2-pyrrolidinone or a lower alkanol such as ethanol, isopropanol or tertiary butanol, at a temperature between room temperature and the reflux temperature of the solvent. The reaction time will depend inter alia on the solvent and the nature of the leaving group, and may be up to 48 hours; however it will typically be from 1 to 24 hours. Suitable leaving groups that L may represent include thioalkyl, sulphonyl, trifluoromethyl sulphonyl, halide, alkyl alcohols, aryl alcohols and tosyl groups; others are recited in 'Advanced Organic Chemistry', J. March (1 985) 3rd Edition, on page 315 and are well known in the art.

In process (b), the reaction is preferably performed by refluxing a mixture of the two compounds for several hours in the presence of a suitable solvent whereby the reaction temperature is high enough so that condensation takes place readily, but not sufficiently high to decompose the amidine formed. The reaction temperature can vary from room temperature to about 250° C., although it is preferable to perform the reaction at temperatures from about 100° C. to 200 ° C. We find that o-dichlorobenzene is a particularly suitable solvent. We also find that it is often useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid. We prefer that HA is a hydrohalic acid.

In process (c) the reaction will take place under standard conditions, for example by reacting the two compounds in an inert solvent such as DMF under basic conditions at a suitable temperature, typically room temperature, for a period of up to 72 hours or until the reaction is complete. We have frequently found it desirable to treat the amine with NaH before reacting with the compound of formula (VI). Suitable leaving groups L are mentioned above. We prefer that L represents halide, particularly bromide.

In process (d), the reaction will typically take place on refluxing the reaction mixture for up to 4 hours or until reaction is complete.

Salts of compounds of formula (I) may be formed by reacting the free base or a salt, enantiomer, tautomer or protected derivative thereof, with one or more equivalents of the appropriate acid. The reaction may be carried out in a solvent or medium in which the salt is insoluble, or in a solvent in which the salt is soluble followed by subsequent removal of the solvent in vacuo or by freeze drying. Suitable solvents include, for example, water, dioxan, ethanol, isopropanol, tetrahydrofuran or diethyl ether, or mixtures thereof. The reaction may be a metathetical process or it may be carried out on an ion exchange resin.

The compounds of formula (II) may be prepared by reduction of a corresponding compound of formula (VII)

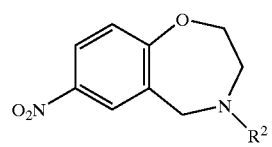

wherein $R^2$ is as defined above.

The reduction reaction may be performed under a number of conditions, for example those described in J. March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure in the presence of a palladium and carbon catalyst until reaction is complete, typically for 3 to 6 hours, or by reduction using zinc metal in acetic acid and methanol.

Compounds of formula (VII) may be prepared by cyclising a compound of formula (VIII)

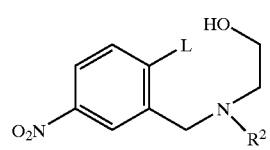

wherein $R^2$ is as defined above and L is a leaving group, preferably fluoro;
or by cyclising a compound of formula (IX)

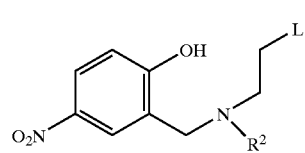

wherein $R^2$ is as defined above and L is a leaving group.

Compounds of formula (VIII) may be prepared by reaction of a compound of formula (X)

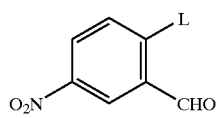

wherein L is a leaving group, preferably fluoro, with a compound of formula (XI)

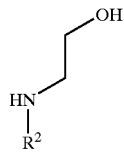

wherein $R^2$ is as defined above, by the process of reductive amination.

Other syntheses of compounds of formula (VIII) and (IX) will be readily apparent to one skilled in the art. Compounds of formula (VIII) or (IX) may cyclise directly to a compound of formula (VII) without the need for prior isolation. The cyclisation reactions may also take place on removal of protecting groups. In the above reactions it may be desirable to render the nucleophilic group —OH in compounds of formula (VIII) and (IX) more reactive by treatment with base.

Compounds of formula (VII) may also be prepared by nitration of a compound of formula (XII)

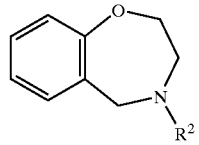

wherein $R^2$ is as defined above.

The nitration reaction will take place under conditions well known to a person skilled in the art, for example, on treatment with nitric acid and sulphuric acid or potassium nitrate and sulphuric acid, optionally in an inert organic solvent.

It may also be convenient to prepare compounds of formula (VII) by nitration of a carbonyl or dicarbonyl derivative of a compound of formula (XII); which nitrated carbonyl or dicarbonyl derivative may be reduced to the desired compound of formula (VII) using, for example, diborane.

Compounds of formula (VII) and (XII), as well as certain carbonyl and dicarbonyl derivatives of compounds of formula (XII) just mentioned may also be prepared by one of the numerous methods for preparation of bicyclic heterocyclic compounds.

Compounds of formula (XII) in which $R^2$ represents hydrogen may also be prepared by a synthesis based on ring expansion to convert a cyclic ketone into a cyclic amide (Grunewald and Dahanukar, *J. Heterocyclic Chem.*, 1994, 31, 1609–1617).

Thus, a compound of formula (XIII)

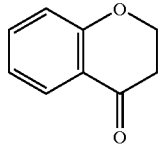

may be converted into a compound of formula (XIV)

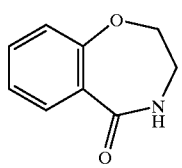

on treatment with sodium azide in acid. Further details of the reaction conditions may be obtained by reference to the above mentioned Grunewald and Dahanukar paper.

It will be apparent to a person skilled in the art that the compounds of formula (XIV) may also desirably be prepared in nitrated form. Nitration may be achieved by treatment of the non-nitrated analogue with nitric acid and sulphuric acid or potassium nitrate and sulphuric acid under standard conditions.

Intermediate compounds may be prepared as such or in protected form. In particular amine and hydroxyl groups may be protected. Suitable protecting groups are described in the standard text "Protective Groups in Organic Synthesis", 2nd Edition (1991) by Greene and Wuts. Amine-protecting groups which may be mentioned include alkyloxycarbonyl such as t-butyloxycarbonyl, phenylalkyloxycarbonyl such as benzyloxycarbonyl, or trifluoroacetate. Deprotection will normally take place on treatment with aqueous base or aqueous acid.

Compounds of formula (VII), (VIII), (IX), (XI) and (XII) in which $R^2$ represents C 1 to 4 alkyl may also be prepared by alkylating the corresponding compound in which $R^2$ represents hydrogen following process (c) above.

Compounds of formula (IV) may be prepared by analogous processes to those described for the preparation of compounds of formula (II). Compounds of formula (IV) may be converted into corresponding compounds of formula (II) by treatment with a base. Compounds of formula (II) may be converted into corresponding compounds of formula (IV) by treatment with a protic acid HA, for example, one of those listed above.

Compounds of formula (III) are either known or may be prepared by known methods. For example, compounds of formula (III) in which L represents thioalkyl may be prepared by treatment of the corresponding thioamide of formula (XV)

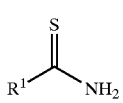

wherein $R^1$ is as defined above, with an alkylhalide under conditions well known to a person skilled in the art.

Alternatively, the acid addition salts of compounds of formula (III) wherein L is thioalkyl may be prepared by reaction of a nitrile of formula (V) with an alkyl thiol and acid, for example hydrochloric acid, in a solvent such as dichloromethane or diethyl ether.

Compounds of formula (V), (VI), (X), (XI), (XIII), (XIV) and (XV) are either known or may be prepared by conventional methods known per se.

It will be apparent to a person skilled in the art that it may be desirable to protect an amine or other reactive group in an intermediate compound using a protecting group as described in the standard text "Protective Groups in Organic Synthesis", 2nd Edition (1991) by Greene and Wuts. Suitable amine-protecting groups are mentioned above.

The compounds of the invention and intermediates may be isolated from their reaction mixtures, and if necessary further purified, by using standard techniques.

The compounds of formula (I) may exist in tautomeric, enantiomeric or diastereoisomeric forms, all of which are included within the scope of the invention. The various optical isomers may be isolated by separation of a racemic mixture of the compounds using conventional techniques, for example, fractional crystallisation or HPLC. Alternatively, the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula (I) possess useful nitric oxide synthase inhibiting activity, and in particular, they exhibit good selectivity for inhibition of the neuronal isoform of nitric oxide synthase. They are thus useful in the treatment or prophylaxis of human diseases or conditions in which the synthesis or oversynthesis of nitric oxide by nitric oxide synthase forms a contributory part. Examples of such diseases or conditions include hypoxia, such as in cases of cardiac arrest, stroke and neonatal hypoxia, neurodegenerative conditions including nerve degeneration and/or nerve necrosis in disorders such as ischaemia, hypoxia, hypoglycemia, epilepsy, and in external wounds (such as spinal cord and head injury), hyperbaric oxygen convulsions and toxicity, dementia, for example, pre-senile dementia, Alzheimer's disease and AIDS-related dementia, Sydenham's chorea, Parkinson's disease, Huntington's disease, Amyotrophic Lateral Sclerosis, Korsakoffs disease, imbecility relating to a cerebral vessel disorder, sleeping disorders, schizophrenia, anxiety, depression, seasonal affective disorder, jet-lag, depression or other symptoms associated with Premenstrual Syndrome (PMS), anxiety and septic shock. The compounds of formula (I) are also useful in the treatment and alleviation of acute or persistent inflammatory or neuropathic pain, or pain of central origin, and in the treatment or prophylaxis of inflammation. Compounds of formula (I) may also be expected to show activity in the prevention and reversal of tolerance to opiates and diazepines, treatment of drug addiction and treatment of migraine and other vascular headaches. The compounds of the present invention may also show useful immunosuppressive activity, and be useful in the treatment of gastrointestinal motility disorders, and in the induction of labour. The compounds may also be useful in the treatment of cancers that express nitric oxide synthase.

Compounds of formula (I) are predicted to be particularly useful in the treatment or prophylaxis of hypoxia or stroke or ischaemia or neurodegenerative conditions or schizophrenia or migraine or for the prevention and reversal of tolerance to opiates and diazepines or for the treatment of drug addiction or for the treatment of pain and especially in the treatment or prophylaxis of hypoxia or stroke or ischaemia or neurodegenerative disorders or schizophrenia or pain. We are particularly interested in conditions selected from the group consisting of hypoxia, ischaemia, stroke, pain, schizophrenia, Parkinson's disease, Huntington's disease and Amyotrophic Lateral Sclerosis.

For the treatment of pain, the compounds of formula (I) are expected to be particularly useful either alone, or in combination with other agents such as opiates, particularly morphine.

For the treatment of Parkinson's disease, the compounds of formula (I) are expected to be particularly useful either alone, or in combination with other agents such as L-Dopa.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

Thus according to a further aspect of the invention we provide a compound of formula (I), or an optical isomer or racemate thereof or a pharmaceutically acceptable salt thereof, for use as a medicament.

According to another feature of the invention we provide the use of a compound of formula (I) or an optical isomer or racemate thereof or a pharmaceutically acceptable salt thereof, in the manufacture of a medicament for the treatment or prophylaxis of the aforementioned diseases or conditions; and a method of treatment or prophylaxis of one of the aforementioned diseases or conditions which comprises administering a therapeutically effective amount of a compound of formula (I), or an optical isomer or racemate thereof or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general, satisfactory results are obtained when the compounds are administered to a human at a daily dosage of between 0.5 mg and 2000 mg (measured as the active ingredient) per day, particularly at a daily dosage of between 2 mg and 500 mg.

The compounds of formula (I), and optical isomers and racemates thereof and pharmaceutically acceptable salts thereof, may be used on their own, or in the form of appropriate medicinal formulations. Administration may be by, but is not limited to, enteral (including oral, sublingual or rectal), intranasal, or topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988.

According to the invention, there is provided a pharmaceutical formulation comprising preferably less than 95% by weight and more preferably less than 50% by weight of a compound of formula (I), or an optical isomer or racemate thereof or a pharmaceutically acceptable salt thereof, in admixture with a pharmaceutically acceptable diluent or carrier. The formulation may optionally also contain a second pharmacologically active ingredient such as L-Dopa, or an opiate analgesic such as morphine.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, that is oesophageal, administration include: tablets, capsules and dragees; sustained release compositions include those in which the active ingredient is bound to an ion exchange resin which is optionally coated with a diffusion barrier to modify the release properties of the resin.

The enzyme nitric oxide synthase has a number of isoforms and compounds of formula (I), and optical isomers and racemates thereof and pharmaceutically acceptable salts thereof, may be screened for nitric oxide synthase inhibiting activity by following procedures based on those of Bredt and Snyder in *Proc. Natl. Acad. Sci.*, 1990, 87, 682–685. Nitric oxide synthase converts $^3$H-L-arginine into $^3$H-L-citrulline which can be separated by cation exchange chromatography and quantified by scintillation counting.

Screen for Neuronal Nitric Oxide Synthase Inhibiting Activity

The enzyme is isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and 25 hydrogen form columns successively, and further centrifugation at 1000 g for 30 seconds.

For the assay, 25 μl of the final supernatant is added to each of 96 wells (of a 96 well filter plate) containing either 25 μl of an assay buffer (50 mM HEPES, 1 mM EDTA, 1.5 mM $CaCl_2$, pH 7.4) or 25 μl of test compound in the buffer at 22° C. and 25 μl of complete assay buffer (50 mM HEPES, 1 mM EDTA, 1.5 mM $CaCl_2$, 1 mM DTT, 100 μM NADPH, 10 μg/ml calmodulin, pH 7.4). Following a 10 minute equilibration period, 25 μl of an L-arginine solution (of concentration 18 μM $^1$H-L-arginine, 96 nM $^3$H-L-arginine) is added to each well to initiate the reaction. The reaction is stopped after 10 minutes by addition of 200 μl of a slurry of termination buffer (20 mM HEPES, 2 mM EDTA, pH 5.5) and Dowex AG-50W-X8 200-400 mesh.

Labelled L-citrulline is separated from labelled L-arginine by filtering each filter plate and 75 μl of each terminated reaction is added to 3 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 80% inhibition of nitric oxide synthase at a concentration of 1 μM, is tested in the assay to verify the procedure.

Screen for Endothelial Nitric Oxide Synthase Inhibiting Activity

The enzyme is isolated from human umbilical vein endothelial cells (HUVECs) by a procedure based on that of Pollock et al in *Proc. Natl. Acad. Sci.*, 1991, 88, 10480–10484. HUVECs were purchased from Clonetics Corp (San Diego, Calif., USA) and cultured to confluency. Cells can be maintained to passage 35–40 without significant loss of yield of nitric oxide synthase. When cells reach confluency, they are resuspended in Dulbecco's phosphate buffered saline, centrifuged at 800 rpm for 10 minutes, and the cell pellet is then homogenised in ice-cold 50 mM Tris-HCl, 1 mM EDTA, 10% glycerol, 1 mM phenylmethylsulphonylfluoride, 2 μM leupeptin at pH 4.2. Following centrifugation at 34,000 rpm for 60 minutes, the pellet is solubilised in the homogenisation buffer which also contains 20 mM CHAPS. After a 30 minute incubation on ice, the suspension is centrifuged at 34,000 rpm for 30 minutes. The resulting supernatant is stored at −80° C. until use.

For the assay, 25 μl of the final supernatant is added to each of 12 test tubes containing 25 μl L-arginine solution (of concentration 12 μM $^1$H-L-arginine, 64 nM $^3$H-L-arginine) and either 25 μl of an assay buffer (50 mM HEPES, 1 mM EDTA, 1.5 mM $CaCl_2$, pH 7.4) or 25 μl of test compound in the buffer at 22° C. To each test tube was added 25 μl of complete assay buffer (50 mM HEPES, 1 mM EDTA, 1.5 mM $CaCl_2$, 1 mM DTT, 100 μM NADPH, 10 μg/ml calmodulin, 12 μM tetrahydrobiopterin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-X8 200-400 mesh column. A 1 ml portion of each terminated reaction mixture is added to an individual I ml column and the eluant combined with that from two 1 ml distilled water washes and 16 ml of scintillation cocktail. The L-citrulline is then quantified by scintillation counting.

In a typical experiment, basal activity is increased by 5,000 dpm/ml of sample above a reagent blank which has an activity of 1500 dprn/ml. A reference standard, N-nitro-L-arginine, which gives 70–90% inhibition of nitric oxide synthetase at a concentration of 1 μM, is tested in the assay to verify the procedure.

In the screens for nitric oxide synthase inhibition activity, compound activity is expressed as $IC_{50}$ (the concentration of drug substance which gives 50% enzyme inhibition in the assay). $IC_{50}$ values for test compounds were initially estimated from the inhibiting activity of 1, 10 and 100 μM solutions of the compounds. Compounds that inhibited the enzyme by at least 50% at 10 μM were re-tested using more appropriate concentrations so that an $IC_{50}$ could be determined.

When tested in the above screens, the compounds of Examples 1 to 7 below showed $lC_{50}$ values for inhibition of neuronal nitric oxide synthase of less than 10 μM and good selectivity for inhibition of the neuronal isoform of the enzyme, indicating that they are predicted to show particularly useful therapeutic activity.

When compared with other compounds, the compounds of formula (I), and optical isomers and racemates thereof and pharmaceutically acceptable salts thereof, have the advantage that they may be less toxic, be more efficacious, be longer acting, have a broader range of activity, be more potent, be more selective for the neuronal isoform of nitric oxide synthase enzyme, produce fewer side effects, be more easily absorbed or have other useful pharmacological properties.

The invention is illustrated by the following examples:

EXAMPLE 1

N-(4-Methyl-2,3,4,5-tetrahydro-1,4-benzoxazepin-7-yl)-2-thiophenecarboximidamide dihydrochloride a) 2-[(2-Fluoro-5-nitrobenzyl)(methyl)amino]ethanol hydrochloride To 2-fluoro-5-nitrobenzaldehyde (6.0 g, 35 inmol) in absolute ethanol (60 ml) was added 2-(methylamino)ethanol (2.9 ml, 35 mmol) and 8M borane-pyridine complex (4.4 ml, 35 mmol). The mixture was stirred for 48 h, concentrated, dissolved in acidic water, and extracted with methylene chloride (3×50 ml). The combined extracts were washed with water, dried over magnesium sulfate, filtered, and concentrated to an oil. The oil was dissolved in isopropanol and treated with isopropanol-HCl. The salt was collected by filtration (2.81 g, 30%), m.p. 163.3–164.8° C.

b) 4-Methyl-7-nitro-2,3,4,5-tetrahydro-1,4-benzoxazepine hydrochloride

To 2-[(2-fluoro-5-nitrobenzyl)(methyl)amino]ethanol (3.3 g, 12 mmol) in DMF (10 ml) was added 60% sodium hydride (1.1 g, 27 mmol). The mixture was heated to 100° C. for 18 h, poured into water, and extracted with ethyl acetate (3×50 ml). The combined extracts were washed with water, dried over magnesium sulfate, filtered, and concentrated to an oil that solidified. The solid was dissolved in isopropanol and treated with isopropanol-HCl. The salt was collected by filtration (1.52 g, 52%), m.p. 233-235° C. dec.

c) 4-Methyl-2,3,4,5-tetrahydro-1,4-benzoxazepin-7-ylamine

4-Methyl-7-nitro-2,3,4,5-tetrahydro-1,4-benzoxazepine (1.52 g, 6.0 mmol) was dissolved in methanol (100 ml) and hydrogenated at 50 psi in the presence of a catalytic quantity of 10% Pd-C. After 1 h the mixture was filtered through glass and evaporated to an oil which was used immediately in the next step.

d) N-(4-Methyl-2,3,4,5-tetrahydro-1,4-benzoxazepin-7-yl)-2-thiophenecarboximidamide dihydrochloride The residue from the preceeding reaction was dissolved in N-methyl-2-pyrrolidinone (10 ml) and to this was added 2-thiophenecarboximidothioic acid, methyl ester, hydroiodide (1.81 g, 6.6 mmol). The mixture was stirred for 24 h at 45° C., poured into basic water and extracted with ethyl acetate (3×100 ml). The combined extracts were washed with water, dried over magnesium sulfate, filtered, and concentrated to a solid which was recrystallized from methylene chloride. The solid was dissolved in ethanol, treated with isopropanol-HCl and triturated with ether. The salt was collected by filtration (0.58 g, 27%), m.p. 172-175° C.

EXAMPLE 2

N-(4-Ethyl-2,3,4,5-tetrahydro-1,4-benzoxazepin-7-yl)-2-thiophenecarboximidamide dihydrochloride Starting with 2-fluoro-5-nitrobenzaldehyde (6.0 g, 35 mmol) and 2-(ethylamino)ethanol (3.2 g, 35 mmol), the title compound was prepared using the process described in Example 1.

M.p. 138–141° C.

EXAMPLE 3

N-(4-Propyl-2,3,4,5-tetrahydro-1,4-benzoxazepin-7-yl)-2-thiophenecarboximidamide hemifumarate a) 2,3,4,5-Tetrahydro-1,4-benzoxazepin-5-one To 4-chromanone (50 g, 340 mmol) in acetic acid (670 ml) was added sodium azide (66.31 g, 1.02 mol) and conc. sulfuric acid (100 ml) dropwise at 0° C. The mixture was heated to 50° C. for 4 h and then cooled to room temperature. The mixture was poured onto ice (1 l) and basified with conc. ammonium hydroxide. The mixture was stirred for 24 h and the solids were collected by filtration (30.43 g, 55%), MS $^m$/z 164 [M+H]$^+$.

b) 7-Nitro-2,3,4,5-tetrahydro-1,4-benzoxazepin-5-one

To 2,3,4,5-tetrahydro-1,4-benzoxazepin-5-one (30.34 g, 190 mmol) in conc. sulfuric acid (600 ml) at 0° C. was added potassium nitrate (20.82 g, 206 mmol) portionwise. The mixture was stirred for 20 minutes at 0° C. and then for 4 h at room temperature. The mixture was poured onto ice (2l) and the solids were collected by filtration. The solids were taken up in hot ethyl acetate and then cooled to yield the title compound (8.79 g, 22%), MS $^m$/z 209 [M+H]$^+$.

c) 7-Nitro-2,3,4,5-tetrahydro-1,4-benzoxazepine hydrochloride

To 7-nitro-2,3,4,5-tetrahydro-1,4-benzoxazepin-5-one (8.79 g, 40 mmol) in THF (100 ml) was added 1M borane-THF complex (130 ml, 130 mmol). The mixture was heated to reflux under nitrogen for 4 h. It was then cooled to 0° C., quenched with 4N HCl (50 ml), and refluxed for an additional 1 h. The mixture was then concentrated, diluted with water (100 ml), basified with 2N NaOH (30 ml), and extracted with ethyl acetate (3×100 ml).

The combined extracts were washed with water, dried over magnesium sulfate, filtered, and concentrated to an oil that crystallized upon standing. The solids were dissolved in methanol and treated with isopropanol-HCl. The salt was collected by filtration (7.92 g, 86%), MS $^m$/z 195 [M+H]$^+$.

d) 2,3,4,5-Tetrahydro-1,4-benzoxazepin-7-ylamine hydrochloride

7-Nitro-2,3,4,5-tetrahydro-1,4-benzoxazepine (5 g) was dissolved in methanol (250 ml) and hydrogenated at 50 psi in the presence of a catalytic quantity of 10% Pd-C. After 1 h the mixture was filtered through glass and evaporated to a solid. The solid was dissolved in hot methanol (20 ml), and treated with isopropanol-HCl and then ether was added until solids formed. The salt was collected by filtration (3.67 g, 85%), MS $^m$/z 165 [M+H]$^+$.

e) N-(2,3,4,5-Tetrahydro-1,4-benzoxazepin-7-yl)-2-thiophenecarboximidamide

To 2,3,4,5-tetrahydro-1,4-benzoxazepin-7-ylamine (3.67 g, 18 mmol) in DMF (60 ml) was added 2-thiophenecarboximidothioic acid, methyl ester, hydroiodide (5.52 g, 19 mmol). The mixture was heated to 50° C. for 24 h. The mixture was poured into water (50 ml), then basic water (150 ml) and was allowed to stir for 1 h. The solids were collected by filtration. The solid was dissolved in hot ethyl acetate, filtered, and diluted with hexane. The solids were collected by filtration (3.13 g, 64%), MS $^m$/Z 274 [M+H]$^+$.

f) N-(4-Propyl-2,3,4,5-tetrahydro-1,4-benzoxazepin-7-yl)-2-thiophenecarboximidamide hemifumarate To N-(2,3,4,5-tetrahydro-1,4-benzoxazepin-7-yl)-2-thiophenecarboximidamide (1.57 g, 6 mmol) in DMF (75 ml) was added potassium carbonate (9 g) and 1-bromopropane (1.48 g, 12 mmol) and a catalytic amount of sodium iodide. The mixture was stirred for 48 h and was then filtered. The solids were dissolved in water (50 ml) and extracted with methylene chloride (3×50 ml). The combined extracts were dried with magnesium sulfate, filtered and concentrated to a solid. The solids were recrystallized from hot isopropanol. The solids were dissolved in ethyl acetate, treated with isopropanol-fumaric acid, and triturated with ether. The hemifumarate salt was collected by filtration (0.86 g, 39%), m.p. 174° C.

EXAMPLE 4

N-(4-Isopropyl-2,3,4,5-tetrahydro-1,4-benzoxazepin-7-yl)-2-thiophenecarboximidamide hemifumarate a) 2-[(2-Fluoro-5-nitrobenzyl)(isopropyl)amino]ethanol oxalate To acetic acid (25.76 ml, 450 mmol) and 2-(isopropylamino)ethanol (51.76 ml, 450 mmol) in dry THF (750 ml) at 0° C. was added 2-fluoro-5-nitrobenzaldehyde (75.88 g, 450 mmol) and sodium triacetoxyborohydride (141.99 g, 670 mmol) portionwise. The reaction was allowed to warm to room temperature and was stirred for 3 h. The mixture was taken up in acidic water and washed with methylene chloride (250 ml), made basic with 50% sodium hydroxide (150 ml) and extracted with methylene chloride (3×250 ml). The extracts were dried with magnesium sulfate, filtered, and concentrated to an oil. The oil was dissolved in 95% ethanol and treated with isopropanol-oxalic acid. The oxalate salt was collected by filtration (31.2 g, 20%), m.p. 106–107° C.

b) 4-Isopropyl-7-nitro-2,3,4,5-tetrahydro-1,4-benzoxazepine

To 2-[(2-fluoro-5-nitrobenzyl)(isopropyl)amino]ethanol (31.2 g, 90 mmol) in DMSO (250 ml) was added 25% sodium hydroxide solution (43.2 g, 270 mmol) and the mixture was allowed to stir for 3 h. The reaction was diluted to twice its volume with water and the solids were collected by filtration. The filtrate was extracted with methylene chloride (3×150 ml), washed with water, dried with magnesium sulfate, filtered, and concentrated to an oil. The solid and the oil were dissolved in hot 95% ethanol, then cooled. The solids were collected by filtration (17.47 g, 68%), MS $^m/z$ 237 [M+H]$^+$.

c) 4-Isopropyl-2,3,4,5-tetrahydro-1,4-benzoxazepin-7-ylamine

To 4-isopropyl-7-nitro-2,3,4,5-tetrahydro-1,4-benzoxazepine (17.46 g) in methanol (1.5 l) was added acetic acid (36 ml) and zinc dust (36 g) portionwise, and the mixture was stirred for 3 h. The mixture was diluted with water (1 l), basified with conc. ammonium hydroxide (250 ml), and extracted with ethyl acetate (5×250 ml). The extracts were dried with magnesium sulfate, filtered and concentrated to an oil (11.34 g, 74%) which was used immediately in the next step.

d) N-(4-Isopropyl-2,3,4,5-tetrahydro-1,4-benzoxazepin-7-yl)-2-thiophenecarboximidamide hemifumarate To 4-isopropyl-2,3,4,5-tetrahydro-1,4-benzoxazepin-7-ylamine (11.34 g, 50 mmol) in 95% ethanol (250 ml)) was added 2-thiophenecarboximidothioic acid, ethyl ester, hydrochloride (13.7 g, 66 mmol) and the reaction was stirred for 24 h. The mixture was concentrated, dissolved in water (250 ml), washed with ethyl acetate (150 ml), made basic with 50% sodium hydroxide, and extracted with ethyl acetate (3×150 ml). Solids were collected by filtration of the extracts. The extracts were then dried with magnesium sulfate, filtered and concentrated to solids. The combined solids were dissolved in hot ethyl acetate (150 ml) and hot filtered. Crystals were collected by filtration (8.26 g). The crystals and fumaric acid (4.2 g) were taken up in hot ethyl acetate (750 ml). The hemifumarate salt was collected by filtration (8.16 g, 44%), MS $^m/z$ 316 [M+H]$^+$.

EXAMPLE 5

N-(2,3,4,5-Tetrahydro-1,4-benzoxazepin-7-yl)-3-thiophenecarboximidamide a) 2-[(2-Fluoro-5-nitrobenzyl)amino]ethanol To 2-fluoro-5-nitrobenzaldehyde (52.4 g, 0.31 mol) in absolute ethanol (500 ml) was added ethanolamine (18.93 g, 0.31 mol) and borane-pyridine complex (31.31 ml, 0.31 mol). The mixture was stirred for 48 h and then evaporated. The residue was acidified with 2.5N hydrochloric acid, extracted with methylene chloride (3×150 ml), and the extracts were discarded. The aqueous phase was basified with 25% aqueous sodium hydroxide and extracted with methylene chloride (4×200 ml). These extracts were washed with saturated brine solution, dried over magnesium sulfate and evaporated to give yellow crystals (37.67 g, 57%), m.p. 98.5–99.5° C.

b) 7-Nitro-2,3,4,5-tetrahydro-1,4-benzoxazepine hydrochloride

To 2-[(2-fluoro-5-nitrobenzyl)amino]ethanol (29.13 g, 136 mmol) in DMSO (680 ml) was added 25% aqueous sodium hydroxide (65.28 g, 408 mmol). The mixture was stirred at room temperature overnight, poured into water (1.5 l), and extracted with methylene chloride (4×800 ml). The combined extracts were washed with water, saturated brine solution, dried over magnesium sulfate, concentrated to a viscous oil, and acidified with 2.5N hydrochloric acid, giving a brown solid (24.58 g, 80%), m.p. 274–276° C.

c) 2,3,4,5-Tetrahydro-1,4-benzoxazepin-7-ylamine hydrochloride

The title compound was obtained from the above 7-nitro-2,3,4,5-tetrahydro-1,4-benzoxazepine hydrochloride by catalytic hydrogenation as described in Example 3(d).

d) 3-Thiophenecarboximidothioic acid, methyl ester, hydroiodide

The title compound was prepared from 3-thiophenecarbothioamide and methyl iodide by a procedure analogous to that described in WO 95/05363, Example 1 (d). M.p. 157–158° C.

e) N-(2,3,4,5-Tetrahydro-1,4-benzoxazepin-7-yl)-3-thiophenecarboximidamide 2,3,4,5-Tetrahydro-1,4-benzoxazepin-7-ylamine hydrochloride (1.84 g, 8.4 mmol) was dissolved in 95% ethanol (40 ml) and 3-thiophenecarboximidothioic acid, methyl ester, hydroiodide (2.85 g, 10 mmol) was added. The mixture was stirred at room temperature for 2 days and then heated at 60° C. overnight and cooled. The solid (1.02 g) was collected. The filtrate was evaporated and the residue treated with ethyl acetate. The resulting crystals were collected and combined with the solid obtained previously. They were dissolved in water (20 ml), basified with conc. ammonium hydroxide, and extracted with methylene chloride (3×30 ml). The organic extracts were washed with water, dried over magnesium sulfate, and concentrated to give a solid (0.508 g), m.p. 150–152° C.

EXAMPLE 6

N-(4-Methyl-2,3,4,5-tetrahydro-1,4-benzoxazepin-7-yl)-3-thiophenecarboximidamide a) 4-Methyl-7-nitro-2,3,4,5-tetrahydro-1,4-benzoxazepine hydrochloride A mixture of 7-nitro-2,3,4,5-tetrahydro-1,4-benzoxazepine hydrochloride (11.53 g, 50 mmol), 37% formaldehyde (25 ml, 335 mmol) and 88% formic acid (15 ml, 340 mmol) was heated at 80° C. for 24 h, cooled and poured into water (150 ml). The suspension was Is basified with 25% aqueous sodium hydroxide to give a brown solid (7.52 g). The aqueous layer was extracted with methylene chloride (3×200 ml), washed with saturated brine solution, and dried over magnesium sulphate to give yellow crystals (1.02 g). This sample was combined with the solid obtained earlier and suspended in isopropanol (750 ml), refluxed for several hours and then filtered. The filtrate was acidified to give the title compound (9.51 g).

b) 4-Methyl-2,3,4,5-tetrahydro-1,4-benzoxazepin-7-ylamine hydrochloride

The product from step (a) above was reduced by catalytic hydrogenation using the process described in Example 1(c) to give the title compound. MS $^m/z$ 179 [M+H]$^+$.

c) N-(4-Methyl-2,3,4,5-tetrahydro-1,4-benzoxazepin-7-yl)-3-thiophenecarboximidamide Using the products from Examples 6(b) and 5(d), the title compound was prepared using the method of Example 5(e). M.p. 255–256° C.

EXAMPLE 7

N-(2,3,4,5-Tetrahydro-1,4-benzoxazepin-7-yl)-2-thiophenecarboximidamide hydrochloride 4-Methyl-2,3,4,5-tetrahydro-1,4-benzoxazepin-7-ylamine hydrochloride (8.7 g, 0.052 mol) and 2-thiophenecarboximidothioic acid, methyl ester, hydroiodide (1 8.0 g, 0.063 mol) in 1-methyl-2-pyrrolidinone (50 ml) were stirred at room temperature for 78 h. The reaction mixture was then poured into water (500 ml) and extracted with ethyl acetate (200 ml). The aqueous phase was then made basic with 50% aqueous sodium hydroxide and extracted with ethyl acetate (2×200 ml). Evaporation of the solvent yielded a crude product which was converted into a hydrochloride salt (9.3 g) using ethanol-HCl. M.p. 269–270° C.

What is claimed is:
1. A compound of formula (I)

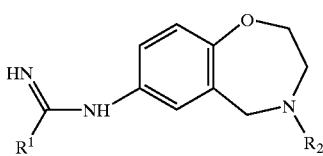

(I)

wherein:
   $R^1$ represents a 2-thienyl or 3-thienyl ring;
   and $R^2$ represents hydrogen or C 1 to 4 alkyl;
   and optical isomers and racemates thereof and pharmaceutically acceptable salts thereof.
2. A compound of formula (I), according to claim 1, wherein $R^1$ represents 2-thienyl.
3. A compound of formula (I), according to claim 1, wherein $R^2$ represents hydrogen, methyl or 2-propyl.
4. A compound of formula (I), according to claim 1, wherein $R^1$ represents 2-thienyl and $R^2$ represents hydrogen, methyl or 2-propyl.
5. A compound of formula (I) which is:
N-(4-methyl-2,3,4,5-tetrahydro-1,4-benzoxazepin-7-yl)-2-thiophenecarboximidamide;
N-(4-ethyl-2,3,4,5-tetrahydro-1,4-benzoxazepin-7-yl)-2-thiophenecarboximidamide;
N-(4propyl-2,3,4,5-tetrahydro-4-benzoxazepin-7-yl)-2-thiophenecarboximidamide;
N-(4-isopropyl-2,3,4,5-tetrahydro-1,4-benzoxazepin-7-yl)-2-thiophenecarboximidamide;
N-(2,3,4,5-tetahydro-1,4-benzoxazepin-7-yl)-2-thiophenecarboximidamide;
N-(2,3,4,5-tetrahydro-1,4-benzoxazepin-7-yl)-3-thiophenecarboximidamide;
N-(4-methyl-2,3,4,5-tetrahydro-1,4-benzoxazepin-7-yl)-3-thiophenecarboximidamide;
or an optical isomer or racemate of any one thereof or a pharmaceutically acceptable salt of any one thereof.
6. A pharmaceutical formulation comprising a compound of formula (I), as defined in claim 1, or an optical isomer or racemate thereof or a pharmaceutically acceptable salt thereof, optionally in admixture with a pharmaceutically acceptable diluent or carrier.
7. A pharmaceutical formulation comprising a compound of formula (I) as defined in claim 1, or an optical isomer or racemate thereof or a pharmaceutically acceptable salt thereof, in combination with L-Dopa, or with an opiate analgesic, optionally in admixture with a pharmaceutically acceptable diluent or carrier.
8. A pharmaceutical formulation according to claim 7 wherein said opiate analgesic is morphine.
9. A method of treating, or reducing the risk of, a human disease or condition in which inhibition of nitric oxide synthase activity is beneficial which comprises administering to a person suffering from or susceptible to such a disease or condition, a therapeutically effective amount of a compound of formula (I), as defined in claim 1, or an optical isomer or racemate thereof or a pharmaceutically acceptable salt thereof.
10. A method of treatment according to claim 9 in which it is predominantly the neuronal isoform of nitric oxide synthase that is inhibited.
11. A method of treating, or reducing the risk of, hypoxia or stroke or ischaemia or neurodegenerative conditions or schizophrenia or pain or migraine, or for the prevention and reversal of tolerance to opiates and diazepines, or for the treatment of drug addiction which comprises administering to a person suffering from or susceptible to such a disease or condition a therapeutically effective amount of a compound of formula (I), as defined in claim 1, or an optical isomer or racemate thereof or a pharmaceutically acceptable salt thereof.
12. A method of treatment according to claim 11, wherein the condition to be treated is selected from the group consisting of hypoxia, ischaemia, stroke, Huntington's disease, Parkinson's disease, Amyotrophic Lateral Sclerosis, schizophrenia and pain.
13. A method of treatment according to claim 12, wherein the condition to be treated is stroke.
14. A method of treatment according to claim 12, wherein the condition to be treated is Amyotrophic Lateral Sclerosis.
15. A method of treatment according to claim 12, wherein the condition to be treated is pain.
16. A method of treatment according to claim 12, wherein the condition to be treated is Huntington's disease.
17. A method of treatment according to claim 12, wherein the condition to be treated is Parkinson's disease.
18. A method of treatment according to claim 12, wherein the condition to be treated is schizophrenia.
19. A method of treatment according to claim 11, wherein the condition to be treated is migraine.
20. A method of treating, or reducing the risk of suffering from, pain which comprises administering to a person suffering from or at risk of suffering from pain, a therapeutically effective amount of a compound of formula (I), as defined in claim 1, or an optical isomer or racemate thereof, or a pharmaceutically acceptable salt thereof, in combination with an opiate analgesic agent.
21. A method according to claim 20 wherein said opiate analgesic agent is morphine.
22. A method of treatment of Parkinson's disease which comprises administering to a person suffering from, or at increased risk of suffering from, Parkinson's disease, a therapeutically effective amount of a compound of formula (I), as defined in claim 1, or an optical isomer or racemate thereof or a pharmaceutically acceptable salt thereof, in combination with L-Dopa.

23. A process for the preparation of a compound of formula (I), as defined in claim 1, and optical isomers and racemates thereof and pharmaceutically acceptable salts thereof, which comprises:

(a) preparing a compound of formula (I) by reacting a corresponding compound of formula (II)

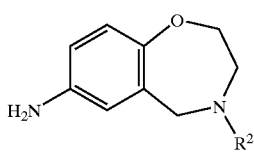

(II)

wherein $R^2$ is as defined in claim 1,
with a compound of formula (III) or an acid addition salt thereof

(III)

wherein $R^1$ is as defined in claim 1 and L is a leaving group;

(b) preparing a compound of formula (I) by reacting a corresponding compound of formula (IV)

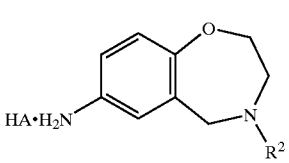

(IV)

wherein $R^2$ is as defined in claim 1 and HA is an acid, with a compound of formula (V)

(V)

wherein $R^1$ is as defined in claim 1;

(c) preparing a compound of formula (I) in which $R^2$ represents C 1 to 4 alkyl by reacting a corresponding compound of formula (I) in which $R^2$ represents hydrogen with a compound of formula (VI)

(VI)

wherein $R^3$ represents C 1 to 4 alkyl and L is a leaving group; or (d) preparing a compound of formula (I) in which $R^2$ represents methyl by reacting a corresponding compound of formula (I) in which $R^2$ represents hydrogen with formaldehyde and formic acid;

and where desired or necessary converting the resultant compound of formula (I), or another salt thereof, into a pharmaceutically acceptable salt thereof, or vice versa, and where desired converting the resultant compound of formula (I) into an optical isomer thereof.

\* \* \* \* \*